United States Patent
Mubarak

(10) Patent No.: US 10,279,065 B1
(45) Date of Patent: May 7, 2019

(54) SAFE INCENSE EVAPORATOR

(71) Applicant: Rashed Marzouq Saif Mubarak, Al Zahra (KW)

(72) Inventor: Rashed Marzouq Saif Mubarak, Al Zahra (KW)

( * ) Notice: Subject to any disclaimer, the term of this patent is extended or adjusted under 35 U.S.C. 154(b) by 0 days.

(21) Appl. No.: 16/202,041

(22) Filed: Nov. 27, 2018

Related U.S. Application Data

(60) Provisional application No. 62/590,666, filed on Nov. 27, 2017.

(51) Int. Cl.
  *A61L 9/03* (2006.01)
  *F24C 15/20* (2006.01)
  *F24C 1/16* (2006.01)

(52) U.S. Cl.
  CPC ........ *A61L 9/03* (2013.01); *F24C 1/16* (2013.01); *F24C 15/2021* (2013.01)

(58) Field of Classification Search
  CPC ..................................... A61L 9/03; F24C 1/16
  See application file for complete search history.

(56) References Cited

U.S. PATENT DOCUMENTS

| | | | |
|---|---|---|---|
| 666,873 A | 1/1901 | Mulkerins | |
| 3,058,178 A * | 10/1962 | Campagna | A47G 33/00 126/59.5 |
| 4,237,097 A | 12/1980 | McDuffie | |
| D445,721 S | 7/2001 | McLeish et al. | |
| 2004/0136888 A1 * | 7/2004 | Shimizu | A61L 9/03 422/305 |
| 2006/0225724 A1 | 10/2006 | Turner | |

FOREIGN PATENT DOCUMENTS

| | | |
|---|---|---|
| CN | 102462903 | 5/2012 |
| CN | 203074206 | 7/2013 |
| JP | 200195672 | 4/2001 |

* cited by examiner

*Primary Examiner* — Sean E Conley
(74) *Attorney, Agent, or Firm* — Richard C. Litman

(57) ABSTRACT

The safe incense evaporator has a bowl, a flat lid covering the bowl, and a cap or dome defining a chamber above the lid. The bowl defines a basin, and a crucible is concentrically seated at the top of the basin. The basin allows water to surround the crucible. Very small orifices are defined in a central area of the lid, and are also defined in the dome to allow the scent of burning incense to leave the evaporator. The crucible is adapted for holding incense coal or charcoal used to burn or heat incense. The evaporator may have a latch holding the cap onto the bowl in case the evaporator tips over onto its side so that the coals or charcoal will be extinguished by the water from the basin. The evaporator may also have a dual latch or lock to prevent children from tampering with the evaporator.

18 Claims, 4 Drawing Sheets

US 10,279,065 B1

SAFE INCENSE EVAPORATOR

CROSS-REFERENCE TO RELATED APPLICATION

This application claims the benefit of U.S. Provisional Patent Application Ser. No. 62/590,666, filed Nov. 27, 2017.

BACKGROUND

1. Field

The disclosure of the present patent application relates to incense burner (or incense evaporator) construction, and more particularly to a safe incense evaporator designed with safety features that reduce risks associated with burning coal or charcoal in an incense burner.

2. Description of the Related Art

Incense evaporators or burners have been commonly used to generate aromatic smoke or vapor by burning coal or charcoal to release the fragrant odor of incense. Incense burners, however, can sometimes be responsible for accidental fires and injury due to the use of burning coals. Fire may result, e.g., from children playing with the incense evaporator, or when the evaporator is accidentally tipped over. Despite their extended time in existence, there have been no improvements directed to the reduction of fire and injury risks.

A variety of constructions have been proposed for incense burners, also known as censers. Such constructions, however, have typically addressed aesthetic and convenience features. Some of these constructions, for example, have provided locations within the incense burner where the incense coal can be extinguished. None of these designs, however, have provided an ability to extinguish coal in incense burners without user intervention.

Thus, a safe incense evaporator solving the aforementioned problems is desired.

SUMMARY

The safe incense evaporator has a bowl, a flat lid covering the bowl, and a cap or dome defining a chamber above the lid. The bowl defines a basin, and a crucible is concentrically seated at the top of the basin. The basin allows water to surround the crucible. Very small orifices are defined in a central area of the lid, and are also defined in the dome to allow the scent of burning incense to leave the evaporator. The crucible is adapted for holding incense coal or charcoal used to burn or heat incense. The evaporator may have a dual latch or dual lock holding the cap onto the bowl in case the evaporator tips over onto its side so that the coals or charcoal will be extinguished by the water from the basin, and also to prevent children from tampering with the evaporator.

The safe incense evaporator may have any decorative external appearance that may be desired. The bowl may be supported above a table or horizontal supporting surface by a pedestal a mounting column, or by a plurality of legs. The evaporator base should be bigger than the dome (cap) in order to increase the gravity for the water to fall as quickly as possible to extinguish the trapped burning coal when the burner has fallen. The evaporator interior may be made from or lined with a substance (e.g., stainless steel) that withstands heat either directly or as conducted by water in the basin surrounding the crucible, and that avoids corrosion that might accumulate because of the water in the basin or by cleaning and servicing. The exterior is made of a material that dissipates heat.

In use, the basin may be filled to the water line indicia with water surrounding the crucible. The crucible may be filled with a base of sand. Incense coal or charcoal may be ignited outside the evaporator and laid in the crucible with tongs or forceps. When the coal (charcoal) is charred, aromatic incense may be laid on the burning coal with the tongs or forceps, and the lid is placed on top to cover the bowl and latched or locked to secure the lid. The scented aroma of the burning incense is released to the surroundings through the orifices in the lid and/or rim of the bowl. It will be understood that the evaporator includes a removable lid that covers the bowl, and also a disk fixed across the bottom of the cap or dome, both having central orifices, the evaporator body being solid and watertight so that when the bowl lid and the cap bottom are approximated, the burning coal is trapped and water is not leaking. If the evaporator is accidentally tipped over onto its side, the burning coal (charcoal) is extinguished by the pool of water in the basin. When the incense has been consumed, the bowl lid may be unlatched and the hot coal may be removed from the crucible with tongs and extinguished external to the evaporator or by dropping the coal in the pool of water in the basin surrounding the incubator. Alternatively, the evaporator may intentionally be laid on its side.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
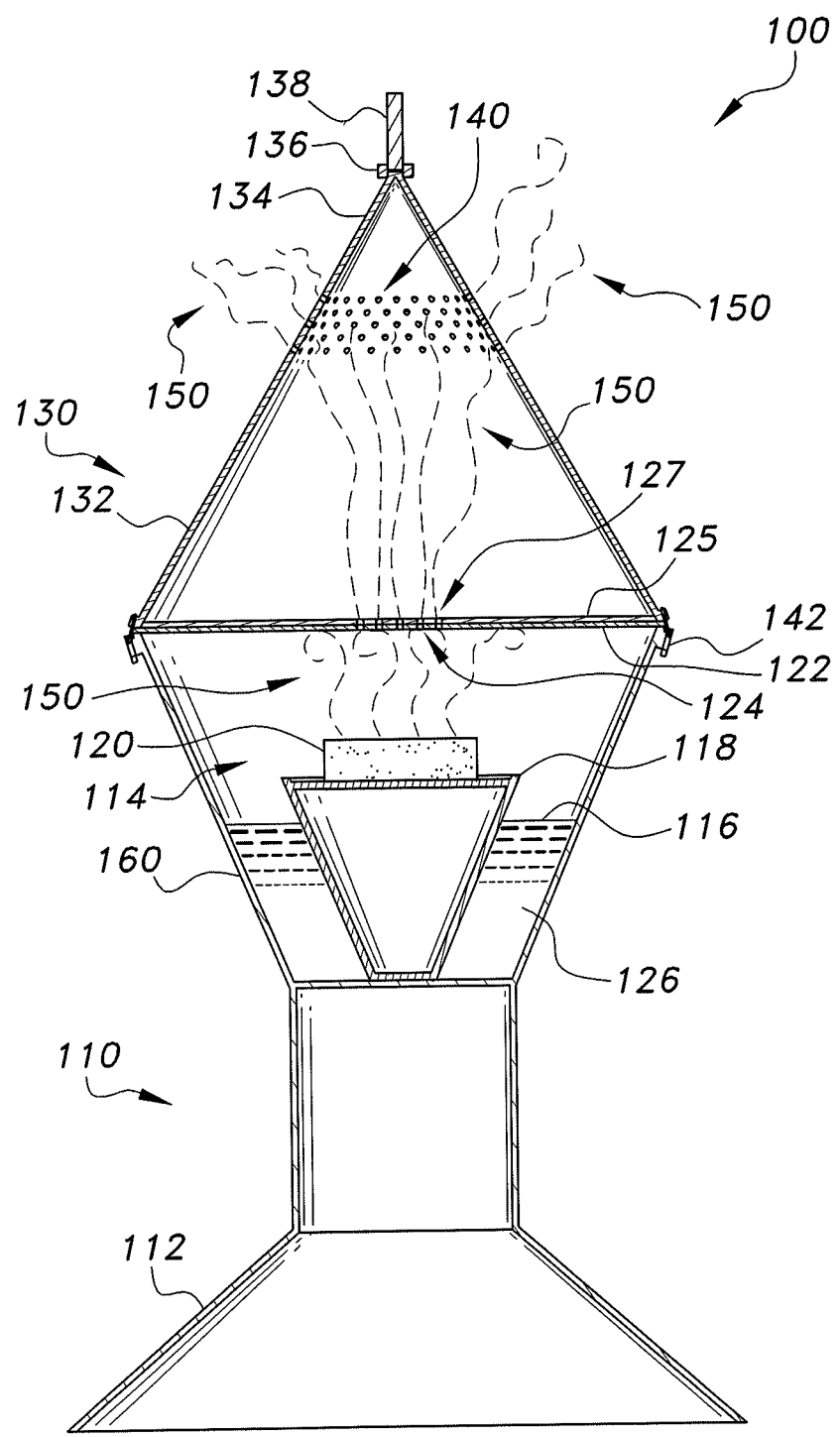
FIG. 1 is a front view in section of an exemplary safe incense evaporator as described herein.

An exemplary embodiment of a safe incense evaporator 100 is shown in FIG. 1. It will be understood that the external shape and configuration of the evaporator 100 shown in the drawings is exemplary only. The evaporator 100 may have any desired external ornamental appearance that would support the features described herein. The safe incense evaporator 100 includes a base 110 and a cap or dome 130. In the exemplary embodiment of FIG. 1, the base 110 includes a pedestal 112 having a short post or column that facilitates placement of the incense evaporator 100 on a flat surface such as a table, desk, counter, etc., while raising the body of the evaporator 100 above the horizontal surface. It will be understood, however, that the base 110 may comprise a plurality of legs or any other structure lifting the body of the evaporator 100 above the supporting horizontal surface. The base 110 should be bigger than the cap or dome 130 in order to increase the gravity for the water to fall as quickly as possible to extinguish the trapped burning coal when the burner has fallen. The base 110 can be constructed of any appropriate material capable of dissipating the heat generated by materials burning inside the incense evaporator 100. For example, various metals (stainless steel, brass, bronze, etc.) or ceramic materials can be used to construct the base 110 due to their ability to withstand high temperatures. The incense evaporator 100 further includes a bowl 114 mounted on the pedestal 112. In the embodiment of FIG. 1, the bowl 114 has the shape of a conical funnel and has a flat removable lid 122 or divider wall disposed over the open top or mouth of the funnel. The lid 122 may be a flat disc disposed on an annular flange or ledge extending around the open mouth of the bowl 114, and secured between the bowl 114 and the fixed lid of the cap 130 when the cap 130 is latched or locked to the bowl 114. The lid 122 may be sealed with a gasket or O-ring to prevent water from leaking out between the bowl 114 and the cover 130 lids if the evaporator is tipped over on its side.

The evaporator 110 includes a crucible 118 that is concentrically disposed at and fixed to the bottom of the bowl 114 (the bowl 114 has a bottom end attached to or defined by the top of the column of the pedestal 112, the top end of the bowl 114 being at the level of the lid 122, the bowl 114 having a frusto-conical sidewall defining the exterior of the lower half of the evaporator 100; the cap 130 is abutted against the lid 122 at the top of the bowl). The crucible 118 is shown having a frusto-conical shape, but is shorter than the bowl 114, being disposed entirely within the bowl 114, with a bottom end fixed to the bottom of the bowl 114 and an open top end below the top end of the bowl 114 but above the water line 116, described below. The bowl 114 defines a basin 160, which is the lower portion of the bowl 114 that surrounds the crucible 118, allowing the crucible 118 to be surrounded by a pool of water 126 that extends up to a water level line 116 marked by indicia disposed on or defined in the bowl 114 below the level of the open top of the crucible 118. Thus, the basin 160 is defined by the bottom of the bowl 114, the frusto-conical sidewall of the bowl 114, and the water level line 116. The crucible 118 may be filled with a base of sand, or any other flame resistant material, and a block of incense coal 120 or charcoal may be ignited and placed on the sand to burn in the crucible 118. Alternatively, the evaporator 100 may include a grate or other support placed across the open top of the crucible 118, and the coal 120 may be placed on the grate or other support. Once the coal (or charcoal) 120 begins to smolder, aromatic incense may be placed on the coal (or charcoal) 120 to burn or vaporize, releasing an aromatic scent. The smoke, fumes, or vapors 150 released by the burning incense travel through small orifices 124 defined in the central area of the lid 122 and small orifices 127 defined in the bottom wall 125 of the cap 130 into a chamber defined by the cap 130, and are released from the chamber to ambient air through small orifices 140 defined in the cap 130.

The cap 130 of the embodiment of the evaporator 100 shown in FIG. 1 also has a conical configuration, the lower end 132 of the cap 130 having a bottom wall 125 having a diameter closely conforming to the diameter of the bowl 114 in order to form a tight seal therewith when the cap 130 is secured to the bowl 114, the bottom wall 125 having small central orifices 127 therein aligned with the orifices 124 defined in the removable lid 122 to permit passage of the aromatic scent of burning incense from the bowl 114 into the chamber defined by the cap 130. The upper end 134 of the cap 130 may have a thermal insulator 136 mounted at the apex, and may have a grip or handle 138 extending therefrom, the grip or handle 138 being made from a material having low thermal conductivity or coated with thermal insulation so that the cap 130 may be gripped and removed by the user without burning the fingers.

The pool of water 126 in the basin 160 surrounding the crucible 118 serves two purposes. First, it helps to cool the bowl 114 of the evaporator 100, dissipating some of the heat generated by burning the incense coal 120 in the crucible. 118. Second, the pool of water 126 in the basin 160 may extinguish the burning coal 120, either by intentionally immersing the coal 120 in the water 126, or because the configuration of the evaporator 100 results in the coal 120 being totally or partially immersed in the pool of water in the evaporator 100 is accidentally tipped over. The safe incense evaporator 100 may be provided with a separate plastic cup (shown as 270 in FIG. 4) marked with calibrated indicia corresponding to the water level line 116 for filling the basin 160 with a preferred premeasured volume of water 126 for accomplishing the two purposes just described. The calibrated volume of water 126 will be adjusted during prototyping to make sure the correct amount of water is provided to extinguish the burning coal, and at the same time, to avoid spillage of excess water out of the burner when the evaporator 100 has fallen.

The embodiment of the evaporator 100 shown in FIG. 1 has two latches or locking mechanisms 142 securing the cap or dome 130 to the bowl 114. The locking mechanisms 142 may be resilient spring clips placed 180° apart that can be rotated to snap or latch the cap 130 to the bowl 114 to secure the two together. The operation may be reversed to unlatch and remove the cap 130 completely from the bowl 114 for servicing the crucible 118 and the basin 160. The bottom wall 125 of the cap 130 and the removable lid 122 may be clamped together atop the bowl 114 between the cap 130 and the bowl 114 when the locking mechanisms are used to secure the cap 130 to the bowl 114, sealing the lid 122 to the bowl 114. The latches 142 are typically sufficient to deter small children from tampering with the safe incense evaporator 100. Also, a single dual lock mechanism may be used.

The safe incense evaporator 100 is configured to reduce and/or eliminate accidental fires that can result from inadvertent toppling thereof by children, pets, adults, natural disasters (e.g., earthquakes), etc. During normal operation, the incense coal 120 is ignited and set to burn on the crucible 118. Smoke 150 emanating from the burning reaction escapes the basin 160 through the orifices 124 formed through the flat removable lid 122 and the orifices 127 in the bottom wall 125 of the cap 130. The smoke 150 subsequently travels into the cap or dome 130 and exits through the orifices 140 in the cap 130. As can be appreciated, during this process, the surface of the incense evaporator 100 can become extremely hot. Furthermore, if the incense evaporator 100 is toppled, the burning incense coal 120 can inadvertently exit the incense evaporator 100, thereby causing a fire or burning a person, child, or pet. Depending on the materials surrounding the incense evaporator 100 when it is toppled, the external surface temperature thereof can also result in burns and/or possible injury. Delicate materials, such as silk tablecloths, for example, can be easily damaged by even low levels heat, which can lead to property fire. Children and pets that come into contact with the incense evaporator can also be subject to injury from burns.

Figure 2:
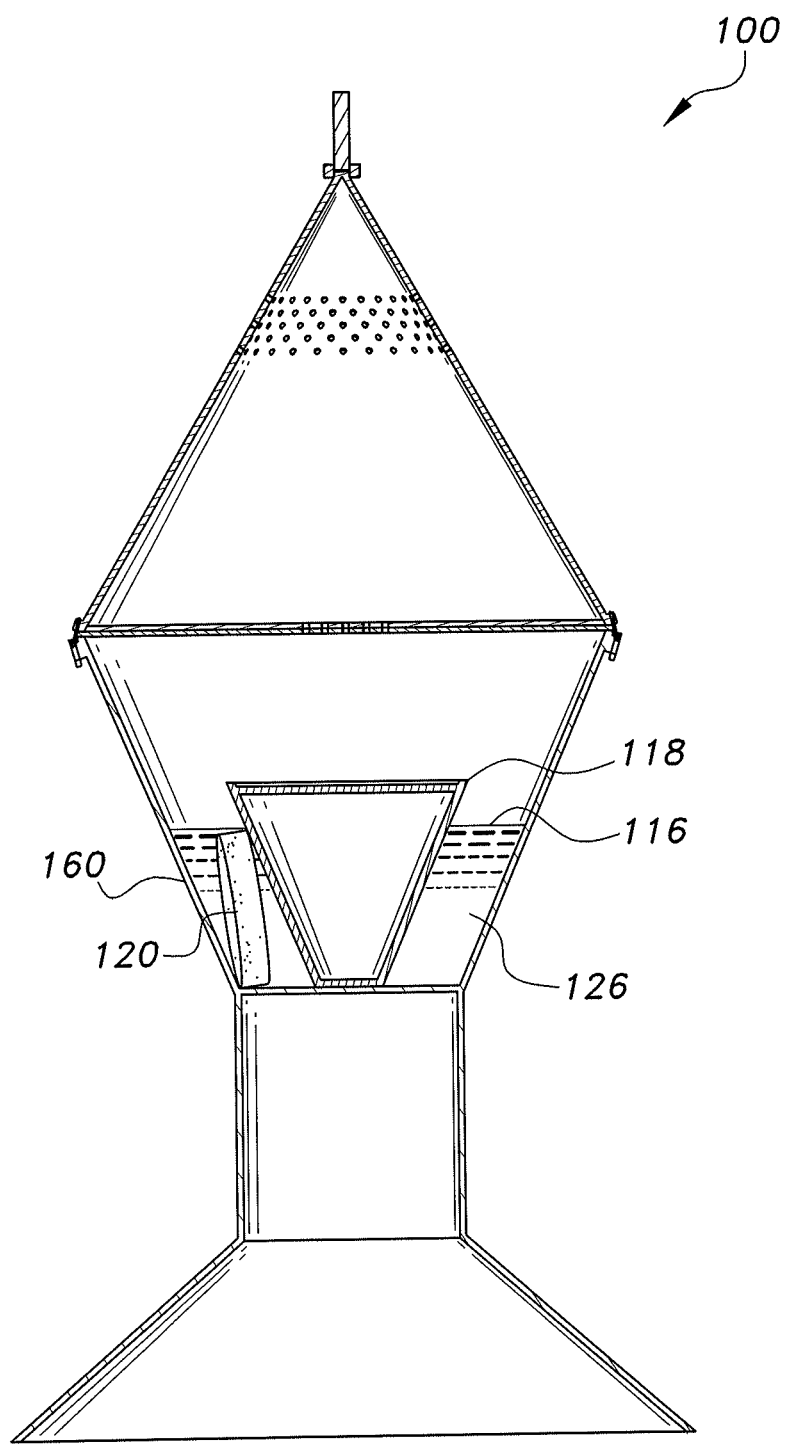
FIG. 2 is an environmental front view in section of the safe incense evaporator of FIG. 1, showing incense coal extinguishment by immersion in water in the basin.

The locking mechanisms 142 secure the cap 132 to the bowl 114 in order to prevent the burning incense coal 120 from exiting the incense evaporator 100. Thus, accidental toppling of the incense evaporator 100 will not result in a fire or burn from direct contact with the incense coal 120. Furthermore, if the incense coal 120 falls from the crucible 118 while burning and the evaporator 100 remains upright, it will land at the bottom of the basin 160. As seen in FIG. 2, the incense coal 120 will become completely submerged in the water 126. The burning incense coal 120 will, therefore, be extinguished without causing any harm. The incense coal 120 may also be intentionally extinguished in this manner when the incense is exhausted by tilting the evaporator 100 to one of its sides or by opening the locking mechanisms 142, removing the cap 130 and lid 122, and using tongs or forceps to lift the coal 120 from the crucible 118 and drop the coal 120 alongside the crucible into the pool of water 126 in the basin 160.

Figure 3:
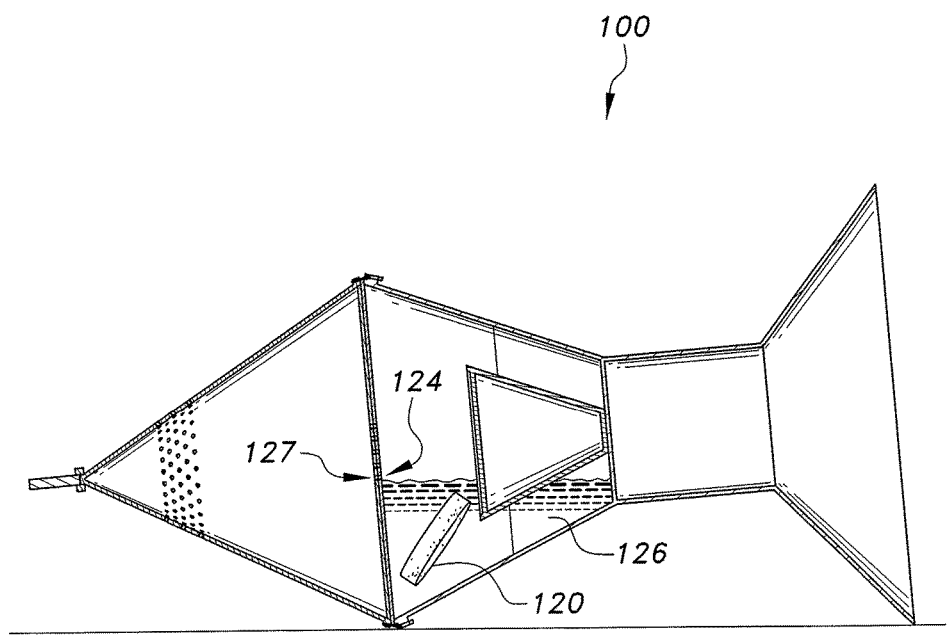
FIG. 3 is an environmental front view in section of the safe incense evaporator of FIG. 1, showing incense coal extinguishment by laying the evaporator on its side.

FIG. 3 illustrates another safety feature of the safe incense evaporator 100. As shown in the illustration, the incense evaporator 100 has been completely toppled onto its side. This can be the result of an accidental bump by a person or pet. Natural disasters such as earthquakes, wind storms, etc. can also cause the incense evaporator 100 to be toppled onto its side. The burning incense coal 120 has been forced off the crucible 118 due to gravity and fallen against the side of the bowl 114. When the evaporator 100 falls on its side, the water 126 shifts into a pool bottomed against the side of the bowl and extending between the lid 122 and the bottom of the bowl. The calibrated amount of water 126 will also be prevented from exiting the incense evaporator 100 due to the lid 122 being sealed between the cap 130 and the bowl 114, which prevents leakage of the water 126. Furthermore, the orifices 124 disposed in the lid 122 are centrally disposed so that the water 126 will remain within the basin portion 114. Although a small amount of water 126 may leak through the small orifices 124 into the chamber defined by the cap or dome 130, a sufficient amount of water 126 will remain within the bowl 114, dammed up by the removable lid 122 and the bottom wall 125 of the cap 130, to extinguish the coal. Accordingly, when the burning incense coal falls from the crucible 118, it will land in the water 126, causing it to be extinguished. The dual-locking mechanism 142 will also prevent the burning incense coal 120 from being accidentally ejected from the incense evaporator 100, where it can injure a person and/or cause a fire.

Figure 4:
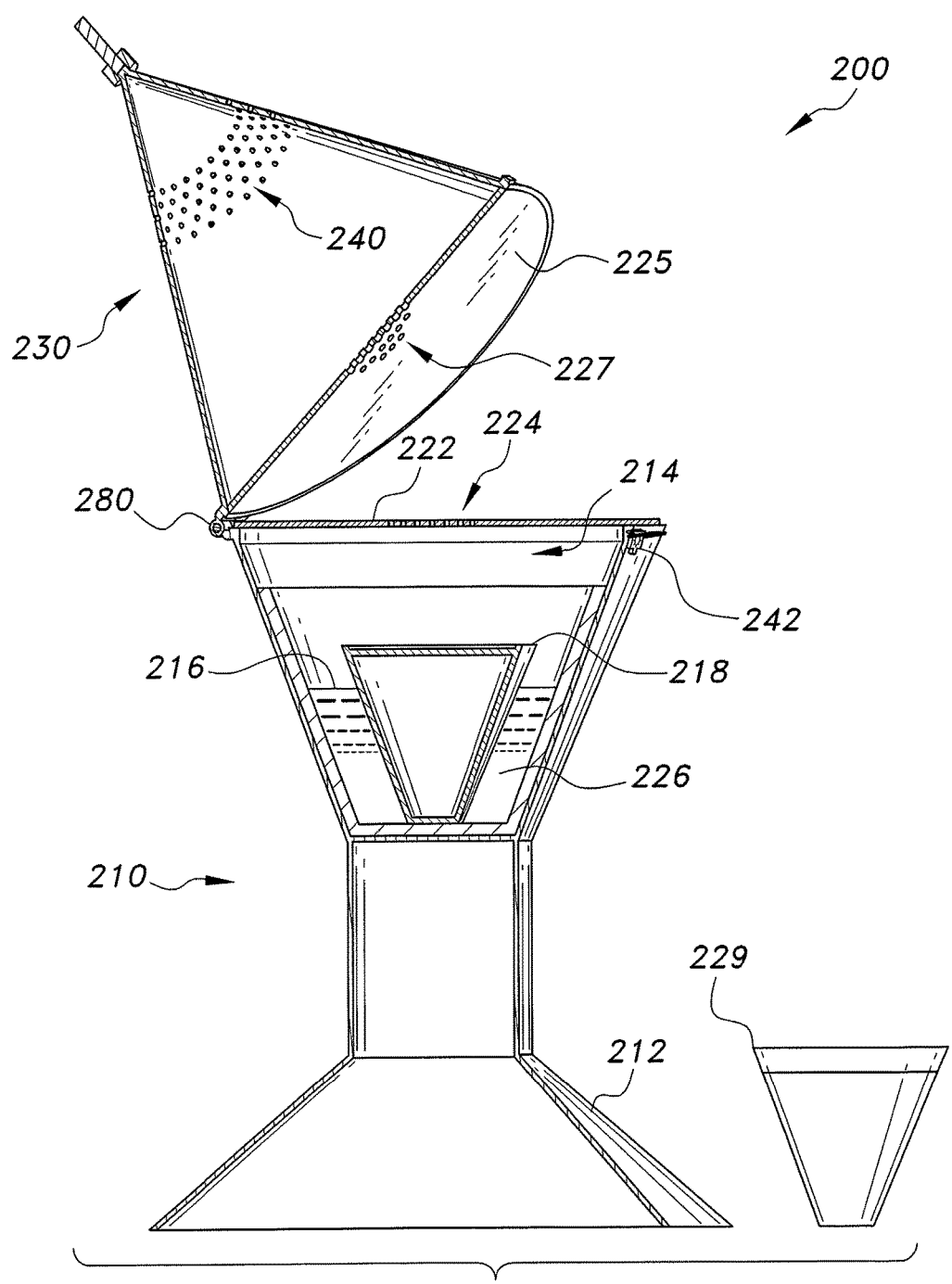
FIG. 4 is a side view, partially in section, of an alternative embodiment of the safe incense evaporator.

FIG. 4 illustrates an alternative embodiment of the incense evaporator 200, which also has a bowl 214 mounted on a base 210 and a cap 230 selectively secured to the bowl 214. The base 210 includes a pedestal 212 to support the incense evaporator 200 when placed on a flat surface. The bowl 214 also is covered by a lid 222 having small orifices 224 defined in its central region. In this embodiment, the diameter of the mouth of the bowl 214 has a smaller profile (or diameter) than the pedestal 212, such that the safe incense evaporator 200 will be tilted at an angle when placed on its side. The lid 222 can be formed as a solid, flat disc that is seated on an annular flange or ledge extending around the mouth of the bowl 214. A sealing material such as a gasket (not shown) can be provided to form a seal and clamp the lid 222 between the cap 230 and the bowl 214.

An indicator line 216 can also be provided on the inner surface of the bowl 214 in order to indicate when a predetermined amount of water 226 has been provided. A receptacle or cup 229 that can further include an indicator line that specifies when an appropriate or correct amount of water 226 may also be provided for filling the evaporator 200. A crucible 218 is concentrically mounted on the bottom of the bowl 214. Although not illustrated, an incense coal or charcoal can be placed on the crucible 218 in the same manner previously described with respect to the crucible 118.

The cap or dome 230 of the incense evaporator 200 includes a first end and a second end, similar to the top described with respect to previous embodiments. As can be seen in FIG. 4, the cap 230 includes a plurality of small orifices 240 for release of aroma from burning incense, a bottom wall 225 having a plurality of central orifices 227, and also includes a single dual-locking mechanism 242. More particularly, a hinge 280 is provided to pivotally secure the cap 230 to the bowl 214. The locking mechanism 242 can subsequently be used to secure the cover 230 to the base 210. As previously discussed, the locking mechanism 242 secures the cap 230 to the base 210 in order to prevent the burning incense coal from accidentally spilling out of the incense evaporator 200. Thus, accidental toppling of the incense evaporator 200 will not result in accidental fire or injury from contact with the burning incense coal. The water 226 in the bowl 214 will instead travel toward the lid 222 and cap 230 and extinguish the burning incense coal. Furthermore, if the burning incense coal falls from the crucible 218 while the incense evaporator 200 is in an upright position, it will land in the pool of water 226 surrounding the crucible 218, where it will become completely submerged. The burning incense coal 220 will, therefore, be extinguished without causing any harm.

It is to be understood that the safe incense evaporator is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A safe incense evaporator, comprising:
    a bowl having a bottom and an open top;
    a crucible concentrically fixed to the bottom of the bowl, the crucible having an open upper end adapted for receiving an incense coal for burning incense, the bowl defining a basin surrounding the crucible adapted for holding a pool of water extending upward towards the open top of the crucible;
    a flat removable lid covering the open top of the bowl, the lid having a central region and a plurality of orifices defined in the central region;
    a cap disposed over the top of the bowl, the cap having a plurality of orifices defined therein and a bottom wall having a plurality of orifices defined therein alignable with the orifices in the removable lid; and
    at least one latch securing the cap to the bowl and sealing the lid between the bowl and the cap, the cap defining a chamber above the lid;
    whereby aroma from incense burning in the crucible leaves the bowl through the aligned orifices in the removable lid and the bottom wall of the cap and exits the chamber above the lid to ambient air through the orifices in the cap; and
    whereby burning incense coals falling out of the crucible when the evaporator is tipped are extinguished in the pool of water.

2. The safe incense evaporator according to claim 1, further comprising a base supporting the bowl, the base being adapted for supporting the evaporator in an upright position on a horizontal support surface.

3. The safe incense evaporator according to claim 2, wherein said base comprises a pedestal and a post extending upward from the pedestal.

4. The safe incense evaporator according to claim 2, wherein said base comprises a plurality of legs extending downward from said bowl.

5. The safe incense evaporator according to claim 2, wherein said base has a larger diameter than the open top of said bowl.

6. The safe incense evaporator according to claim 1, further comprising a calibrated water level line disposed on said bowl below a level even with the open top of said crucible to aid in filling the basin with water, and a small plastic cup provided with a fill line indicated on it.

7. The safe incense evaporator according to claim 1, wherein the basin is calibrated to hold 50 milliliters of water.

8. The safe incense evaporator according to claim 1, wherein said at least one latch comprises a single latch, the evaporator further comprising a hinge connecting said cap to said bowl opposite the single latch.

9. The safe incense evaporator according to claim 1, wherein said at least one latch comprises a pair of latches disposed on opposite sides of said bowl.

10. The safe incense evaporator according to claim 1, wherein said bowl and said lid define a pool for the water extending between the lid and the bottom of the bowl deep enough to submerge a burning incense coal when the evaporator is accidentally tipped over on its side.

11. The safe incense evaporator according to claim 1, wherein said at least one latch provides a watertight seal when the cap is secured to said bowl so that water does not leak out between the cap and said bowl when the evaporator is tipped over sideways.

12. The safe incense evaporator according to claim 1, wherein said cap, said bowl, and said lid are made from stainless steel.

13. The safe incense evaporator according to claim 1, wherein said cap, said bowl, and said lid are made from a metal selected from the group consisting of stainless steel, brass, and bronze.

14. The safe incense evaporator according to claim 1, wherein said cap and said bowl are lined with a metal selected from the group consisting of stainless steel, brass, and bronze.

15. The safe incense evaporator according to claim 1, wherein said bowl has a conical filter shape and said cap is cone-shaped.

16. The safe incense evaporator according to claim 14, wherein said crucible has a conical filter shape.

17. An incense evaporator, comprising a container having:
a burner chamber, including:
a basin having a floor;
a crucible adapted for burning incense, the crucible being concentrically mounted in the basin and fixed to the floor of the basin, the crucible having a lower portion, the basin defining a well around the lower portion of the crucible; and
water disposed within the well;
an aroma chamber, including a cover mounted over the basin, the cover having a plurality of vent holes defined therein for releasing the aroma of the burning incense to ambient air;
a divider wall selectively disposed between the burner chamber and the aroma chamber, the divider wall having a plurality of centrally disposed inter-chamber air passages defined therein for passage of the aroma of burning incense from the burner chamber to the aroma chamber, the divider wall defining the largest diameter of the evaporator; and
at least one latch securing and sealing the cover to the basin with a watertight seal and the divider wall disposed between the chambers;
whereby a burning incense coal is extinguished in the water well when the burning intense coal falls out of the crucible.

18. The incense evaporator according to claim 17, wherein said further aroma chamber further comprises a bottom wall having a plurality of centrally disposed inter-chamber air passages defined therein aligned with the plurality of centrally disposed inter-chamber air passages defined in said divider wall.

* * * * *